US005614367A

United States Patent [19]

Kaluza et al.

[11] Patent Number: 5,614,367
[45] Date of Patent: Mar. 25, 1997

[54] DIAGNOSTIC TEST USING CHIMERIC ANTIBODIES

[75] Inventors: Brigitte Kaluza, Habach; Helmut Lenz, Tutzing, both of Germany

[73] Assignee: Boehringer Mannheim GmbH, Mannheim-Waldhof, Germany

[21] Appl. No.: 154,738

[22] Filed: Nov. 17, 1993

Related U.S. Application Data

[63] Continuation of Ser. No. 948,073, Sep. 21, 1992, abandoned, which is a continuation of Ser. No. 459,481, Jan. 2, 1990, abandoned.

[30] Foreign Application Priority Data

Jan. 10, 1989 [DE] Germany ............................ 39 00 534.8

[51] Int. Cl.$^6$ ................. G01N 33/53; G01N 33/537; C12P 21/08; C12P 21/04
[52] U.S. Cl. ................. 435/7.1; 435/7.94; 435/7.92; 435/69.6; 530/387.3; 530/388.85; 436/500
[58] Field of Search ................. 435/7.1, 7.94, 435/7.92, 69.6; 536/387.3, 388.85; 436/500

[56] References Cited

FOREIGN PATENT DOCUMENTS

| 2007336 | 7/1990 | Canada . | |
|---|---|---|---|
| 0266663 | 5/1988 | European Pat. Off. . | |
| 0274394 | 7/1988 | European Pat. Off. . | |
| 0323806 | 7/1989 | European Pat. Off. . | |
| WO86/01533 | 3/1986 | WIPO . | |
| 9007861 | 7/1990 | WIPO | C12P 21/00 |
| 9116627 | 10/1991 | WIPO | G01N 33/53 |

OTHER PUBLICATIONS

Thompson et al., "Circulating Antibodies To Mouse . . . ," Clin Chem 32:476–481 (1986).
Vaidya et al., "Elimination of Interference . . . ," Oakridge Conf., Apr. 23–24 (1993).
Hama Survey Group, "Survey of Methods . . . ," Clinica Chimica Acta 215: 153–163 (1993).
Harris et al., "Therapeutic Antibodies—The Coming of Age," Tibtech 11:42–44 (1993).
Waldmann, TA, "Monoclonal Antibodies in Diagnosis and Therapy," Science 252: 1657–1662 (1991).
Courtneay–Luck et al., "Preexisting Human Anti–Murine . . . ," Cancer Res 47:4520–4525 (1987).
Morrison, SL, "In Vitro Antibodies," Ann Rev Immunol 10:239, 244, 245 (1992).
Boerman et al., "Heterophilic Antibodies in Human Sera . . . ," Clin Chem 36:888–891 (1990).
Weber et al., "Endogenous Interference in Immunoassays . . . ," Scand J Clin Lab Invest 50, Suppl 201:77–82 (1990).
Verhoeyen et al., "Engineering of Antibodies," BioEssays 8:74–78 (1988).
Iijima et al., "Highly Specific Enzyme Immunoassay For The B–Subunit of Human Thyrotropin . . . ," Clin Chem 34:98–102 (1988).
Primus et al., "'Sandwich'–Type Immunoassay of Carcinoembryonic Antigen in Patients . . . ," Clin Chem 34:261–264 (1988).
Kahn et al., "Factitious Elevation of Thyrotropin In A New Ultrasensitive . . . ," J Clin Endo Metab 66:526–533 (1988).
Beidler et al., "Cloning and High Level Expression Of A Chimeric Antibody . . . ," J Immunol 141:4053–60 (1988).
Koshe et al., "Antibodies as a source of Analytical Errors," J. Clin Chem Biochem. 28, 881–892 (1990).
Boscato et al., "Heterophilic Antibodies: A Problem for all Immunoassays," Clin Chem 34 27–33 (1988).
Verhoeyen et al., "Reshaping Human Antibodies: Grafting an Antilysozyime Activity," Science 239, 1534–36 (1988).
Hansen, H. J., et al., "Solving the Problem of Anitbody Interference in Commercial Sandwich–Type Immunoassays of Carcinoembryonic Antigen" *Clinical Chemistry*, vol. 35, No. 1, 1989, pp. 146–151.

*Primary Examiner*—Michael P. Woodward
*Attorney, Agent, or Firm*—Nikaido, Marmelstein, Murray & Oram, LLP

[57] ABSTRACT

Chimeric monoclonal antibodies or fragments thereof are used according to the present invention in diagnostic tests for the quantitative immunological determination of substances in the blood or serum of patients. For the diagnostic detection of substances in serum or blood of patients by binding of two monoclonal antibodies $R_1$ and $R_2$ directed against the substance, of which the first antibody $R_1$ is capable of binding to a solid phase or is already bound and the second antibody $R_2$ carries a label, binding of the antibody $R_1$ to the solid phase if desired, separation of the complex formed of $R_1$, substance and $R_2$ which is bound to the solid phase and detection via the labelling of the antibody $R_2$, a chimeric monoclonal antibody or a fragment thereof is used at least for one of the antibodies $R_1$ or $R_2$.

8 Claims, 13 Drawing Sheets

FIG.1

```
  1  GATGTTGTGATGACCCAGACTCCACTCACTTTGTCGGTTACCATTGGACAACCAGCCTCC
     AspValValMetThrGlnThrProLeuThrLeuSerValThrIleGlyGlnProAlaSer

61  ATCTCTTGCAAGTCAAGTCAGAGCCTCTTAGATAGTGATGGAAGGACATATTTGAATTGG
     IleSerCysLysSerSerGlnSerLeuLeuAspSerAspGlyArgThrTyrLeuAsnTrp

121  TTGTTACAGAGGCCAGGCCAGTCTCCAAAGCGCCTAATCTATCTGGTGTCTAAACTGGAC
     LeuLeuGlnArgProGlyGlnSerProLysArgLeuIleTyrLeuValSerLysLeuAsp

181  TCTGGAGTCCCTGACAGGTTCACTGGCAGTGGATCAGGGACAGATTTCATACTGAAAATT
     SerGlyValProAspArgPheThrGlySerGlySerGlyThrAspPheIleLeuLysIle

241  AGCAGAGTGGAGGCTGAGGATTTGGGAGCTTATTATTGCTGGCAAGGTACACATTTTCCT
     SerArgValGluAlaGluAspLeuGlyAlaTyrTyrCysTrpGlnGlyThrHisPhePro

301  CAGACNTTCGGTGGAGGCACCAAGCTGGAAATCAAACGGGCTGATGCTGCACCAACTGTA
     GlnThrPheGlyGlyGlyThrLysLeuGluIleLysArgAlaAspAlaAlaProThrVal

361  TCCATCTTCCCACCATCCAGTGAGCAGTTAACATCTGGAGGTGCCTCAGTCGTGTGCTTC
     SerIlePheProProSerSerGluGlnLeuThrSerGlyGlyAlaSerValValCysPhe

421  TTGAACAACTTCTACCCCAAAGACATCAATGTCAAGTGGAAGATTGATGGCAGTGAACGA
     LeuAsnAsnPheTyrProLysAspIleAsnValLysTrpLysIleAspGlySerGluArg

481  CAAAATGGCGTCCTGAACAGTTGGACTGATCAGGACAGCAAAGACAGCACCTACAGCATG
     GlnAsnGlyValLeuAsnSerTrpThrAspGlnAspSerLysAspSerThrTyrSerMet

541  AGCAGCACCCTCACGTTGACCAAGGACGAGTATGAACGACATAACAGCTATACCTGTGAG
     SerSerThrLeuThrLeuThrLysAspGluTyrGluArgHisAsnSerTyrThrCysGlu

601  GCCACTCACAAGACATCAACTTCACCCATTGTCAAGAGCTTCAACAGGAATGAGTGTTAG
     AlaThrHisLysThrSerThrSerProIleValLysSerPheAsnArgAsnGluCysEnd
```

FIG. 2

```
  1  GATGTGCAGCTTCAGGAGTCAGGACCTGACCTGGTGAAACCTTCTCAGTCACTTTCACTC
     AspValGlnLeuGlnGluSerGlyProAspLeuValLysProSerGlnSerLeuSerLeu

61  ACTTGCACTGTCACTGGCTACCCCATCACCAGTGGTTATACCTGGCACTGGATCCGGCAG
     ThrCysThrValThrGlyTyrProIleThrSerGlyTyrThrTrpHisTrpIleArgGln

121  TTTCCAGGAAACTGTCTGGAATGGATGGGCTACATGCACTACAATGGTAGCACTAACTAC
     PheProGlyAsnCysLeuGluTrpMetGlyTyrMetHisTyrAsnGlySerThrAsnTyr

181  AACCCATCTCTCAAAAGTCGAATCTCTATCACTCGAGACACATCCAAGAACCAGTTCTTC
     AsnProSerLeuLysSerArgIleSerIleThrArgAspThrSerLysAsnGlnPhePhe

241  CTGCAGTTGAATTCTGTGACTACTGAGGACACAGCCACATATTACTGTGAATTCTCCTCT
     LeuGlnLeuAsnSerValThrThrGluAspThrAlaThrTyrTyrCysGluPheSerSer

301  ATTATATGGGACTACTGGGGTCAAGGAACCTCAGTCACCGTCTCCTCAGCCAAAACGACA
     IleIleTrpAspTyrTrpGlyGlnGlyThrSerValThrValSerSerAlaLysThrThr

361  CCCCCATCTGTCTATCCACTGGCCCCTGGATCTGCTGCCCAAACTAACTCCATGGTGACC
     ProProSerValTyrProLeuAlaProGlySerAlaAlaGlnThrAsnSerMetValThr

421  CTGGGATGCCTGGTCAAGGGCTATTTCCCTGAGCCAGTGACAGTGACCTGGAACTCTGGA
     LeuGlyCysLeuValLysGlyTyrPheProGluProValThrValThrTrpAsnSerGly

481  TCCCTGTCCAGCGGTGTGCACACCTTCCCAGCTGTCCTGCAGTCTGACCTCTACACTCTG
     SerLeuSerSerGlyValHisThrPheProAlaValLeuGlnSerAspLeuTyrThrLeu

541  AGCAGCTCAGTGACTGTCCCCTCCAGCACCTGGCCCAGCGAGACCGTCACCTGCAACGTT
     SerSerSerValThrValProSerSerThrTrpProSerGluThrValThrCysAsnVal

601  GCCCACCCGGCCAGCAGCACCAAGGTGGACAAGAAAATTGTGCCCAGGGATTGTGGTTGT
     AlaHisProAlaSerSerThrLysValAspLysLysIleValProArgAspCysGlyCys

661  AAGCCTTGCATATGTACAGTCCCAGAAGTATCATCTGTCTTCATCTTCCCCCCAAAGCCC
     LysProCysIleCysThrValProGluValSerSerValPheIlePheProProLysPro

721  AAGGATGTGCTCACCATTACTCTGACTCCTAAGGTCACGTGTGTTGTGGTAGACATCAGC
     LysAspValLeuThrIleThrLeuThrProLysValThrCysValValValAspIleSer

781  AAGGATGATCCCGAGGTCCAGTTCAGCTGGTTTGTAGATGATGTGGAGGTGCACACAGCT
     LysAspAspProGluValGlnPheSerTrpPheValAspAspValGluValHisThrAla

841  CAGACGCAACCCCGGGAGGAGCAGTTCAACAGCACTTTCCGCTCAGTCAGTGAACTTCCC
     GlnThrGlnProArgGluGluGlnPheAsnSerThrPheArgSerValSerGluLeuPro

901  ATCATGCACCAGGACTGGCTCAATGGCAAGGAGTTCAAATGCAGGGTCAACAGTGCAGCT
     IleMetHisGlnAspTrpLeuAsnGlyLysGluPheLysCysArgValAsnSerAlaAla

961  TTCCCTGCCCCCATCGAGAAAACCATCTCCAAAACCAAAGGCAGACCGAAGGCTCCACAG
     PheProAlaProIleGluLysThrIleSerLysThrLysGlyArgProLysAlaProGln

1021 GTGTACACCATTCCACCTCCCAAGGAGCAGATGGCCAAGGATAAAGTCAGTCTGACCTGC
     ValTyrThrIleProProProLysGluGlnMetAlaLysAspLysValSerLeuThrCys
```

FIG.2
continued

1081 ATGATAACAGACTTCTTCCCTGAAGACATTACTGTGGAGTGGCAGTGGAATGGGCAGCCA
     MetIleThrAspPhePheProGluAspIleThrValGluTrpGlnTrpAsnGlyGlnPro

1141 GCGGAGAACTACAAGAACACTCAGCCCATCATGAACACGAATGGCTCTTACTTCGTCTAC
     AlaGluAsnTyrLysAsnThrGlnProIleMetAsnThrAsnGlySerTyrPheValTyr

1201 AGCAAGCTCAATGTGCAGAAGAGCAACTGGGAGGCAGGAAATACTTTCACCTGCTCTGTG
     SerLysLeuAsnValGlnLysSerAsnTrpGluAlaGlyAsnThrPheThrCysSerVal

1261 TTACATGAGGGCCTGCACAACCACCATACTGAGAAGAGCCTCTCCCACTCTCCTGGTAAA
     LeuHisGluGlyLeuHisAsnHisHisThrGluLysSerLeuSerHisSerProGlyLys

1321 TGATCCCAGTGTCCTTGGAGCCCTCTGGTCCTACAGGACTCTGACACCTACCTCCACCCC
     EndSerGlnCysProTrpSerProLeuValLeuGlnAspSerAspThrTyrLeuHisPro

1381 TCCCTGTATAAATAA 1395
     SerLeuTyrLysEnd

FIG. 3

```
  1  GATATCGTGATGACCCAGACTCCACTCACTTTGTCGGTTACCATTGGACAACCAGCCTCC
     AspIleValMetThrGlnThrProLeuThrLeuSerValThrIleGlyGlnProAlaSer

61  ATCTCTTGCAAGTCAAGTCAGAGCCTCTTAGATAGTGATGGAAGGACATATTTGAATTGG
     IleSerCysLysSerSerGlnSerLeuLeuAspSerAspGlyArgThrTyrLeuAsnTrp

121  TTGTTACAGAGGCCAGGCCAGTCTCCAAAGCGCCTAATCTATCTGGTGTCTAAACTGGAC
     LeuLeuGlnArgProGlyGlnSerProLysArgLeuIleTyrLeuValSerLysLeuAsp

181  TCTGGAGTCCCTGACAGGTTCACTGGCAGTGGATCAGGGACAGATTTCATACTGAAAATT
     SerGlyValProAspArgPheThrGlySerGlySerGlyThrAspPheIleLeuLysIle

241  AGCAGAGTGGAGGCTGAGGATTTGGGAGCTTATTATTGCTGGCAAGGTACACATTTTCCT
     SerArgValGluAlaGluAspLeuGlyAlaTyrTyrCysTrpGlnGlyThrHisPhePro

301  CAGACNTTCGGTGGAGGCACCAAGCTCGAGATCAAACGAACTGTGGCTGCACCATCTGTC
     GlnThrPheGlyGlyGlyThrLysLeuGluIleLysArgThrValAlaAlaProSerVal

361  TTCATCTTCCCGCCATCTGATGAGCAGTTGAAATCTGGAACTGCCTCTGTTGTGTGCCTG
     PheIlePheProProSerAspGluGlnLeuLysSerGlyThrAlaSerValValCysLeu

421  CTGAATAACTTCTATCCCAGAGAGGCCAAAGTACAGTGGAAGGTGGATAACGCCCTCCAA
     LeuAsnAsnPheTyrProArgGluAlaLysValGlnTrpLysValAspAsnAlaLeuGln

481  TCGGGTAACTCCCAGGAGAGTGTCACAGAGCAGGAGAGCAAGGACAGCACCTACAGCCTC
     SerGlyAsnSerGlnGluSerValThrGluGlnGluSerLysAspSerThrTyrSerLeu

541  AGCAGCACCCTGACGCTGAGCAAAGCAGACTACGAGAAACACAAAGTCTACGCCTGCGAA
     SerSerThrLeuThrLeuSerLysAlaAspTyrGluLysHisLysValTyrAlaCysGlu

601  GTCACCCATCAGGGCCTGAGCTCGCCCGTCACAAAGAGCTTCAACAGGGGAGAGTGTTAG
     ValThrHisGlnGlyLeuSerSerProValThrLysSerPheAsnArgGlyGluCysEnd
```

FIG. 4

```
  1  GAGGTCCAGCTGCAAGAGTCAGGACCTGACCTGGTGAAACCTTCTCAGTCACTTTCACTC  6
     GluValGlnLeuGlnGluSerGlyProAspLeuValLysProSerGlnSerLeuSerLeu

61  ACTTGCACTGTCACTGGCTACCCCATCACCAGTGGTTATACCTGGCACTGGATCCGGCAG  1
     ThrCysThrValThrGlyTyrProIleThrSerGlyTyrThrTrpHisTrpIleArgGln

121  TTTCCAGGAAACTGTCTGGAATGGATGGGCTACATGCACTACAATGGTAGCACTAACTAC  1
     PheProGlyAsnCysLeuGluTrpMetGlyTyrMetHisTyrAsnGlySerThrAsnTyr

181  AACCCATCTCTCAAAAGTCGAATCTCTATCACTCGAGACACATCCAAGAACCAGTTCTTC  2
     AsnProSerLeuLysSerArgIleSerIleThrArgAspThrSerLysAsnGlnPhePhe

241  CTGCAGTTGAATTCTGTGACTACTGAGGACACAGCCACATATTACTGTGAATTCTCCTCT  3
     LeuGlnLeuAsnSerValThrThrGluAspThrAlaThrTyrTyrCysGluPheSerSer

301  ATTATATGGGACTACTGGGGTCAAGGAACCTCAGTCACCGTCTCTGCAGCCTCCACCAAG  3
     IleIleTrpAspTyrTrpGlyGlnGlyThrSerValThrValSerAlaAlaSerThrLys

361  GGCCCATCGGTCTTCCCCCTGGCACCCTCCTCCAAGAGCACCTCTGGGGGCACAGCGGCC  4
     GlyProSerValPheProLeuAlaProSerSerLysSerThrSerGlyGlyThrAlaAla

421  CTGGGCTGCCTGGTCAAGGACTACTTCCCCGAACCGGTGACGGTGTCGTGGAACTCAGGC  4
     LeuGlyCysLeuValLysAspTyrPheProGluProValThrValSerTrpAsnSerGly

481  GCCCTGACCAGCGGCGTGCACACCTTCCCGGCTGTCCTACAGTCCTCAGGACTCTACTCC  5
     AlaLeuThrSerGlyValHisThrPheProAlaValLeuGlnSerSerGlyLeuTyrSer

541  CTCAGCAGCGTGGTGACCGTGCCCTCCAGCAGCTTGGGCACCCAGACCTACATCTGCAAC  6
     LeuSerSerValValThrValProSerSerSerLeuGlyThrGlnThrTyrIleCysAsn

601  GTGAATCACAAGCCCAGCAACACCAAGGTGGACAAGAAAGTTGAGCCCAAATCTTGTGAC  6
     ValAsnHisLysProSerAsnThrLysValAspLysLysValGluProLysSerCysAsp

661  AAAACTCACACATGCCCACCGTGCCCAGCACCTGAACTCCTGGGGGGACCGTCAGTCTTC  7
     LysThrHisThrCysProProCysProAlaProGluLeuLeuGlyGlyProSerValPhe

721  CTCTTCCCCCCAAAACCCAAGGACACCCTCATGATCTCCCGGACCCCTGAGGTCACATGC  7
     LeuPheProProLysProLysAspThrLeuMetIleSerArgThrProGluValThrCys

781  GTGGTGGTGGACGTGAGCCACGAAGACCCTGAGGTCAAGTTCAACTGGTACGTGGACGGC  8
     ValValValAspValSerHisGluAspProGluValLysPheAsnTrpTyrValAspGly

841  GTGGAGGTGCATAATGCCAAGACAAAGCCGCGGGAGGAGCAGTACAACAGCACGTACCGG  9
     ValGluValHisAsnAlaLysThrLysProArgGluGluGlnTyrAsnSerThrTyrArg

901  GTGGTCAGCGTCCTCACCGTCCTGCACCAGGACTGGCTGAATGGCAAGGAGTACAAGTGC  9
     ValValSerValLeuThrValLeuHisGlnAspTrpLeuAsnGlyLysGluTyrLysCys

961  AAGGTCTCCAACAAAGCCCTCCCAGCCCCCATCGAGAAAACCATCTCCAAAGCCAAAGGG  1
     LysValSerAsnLysAlaLeuProAlaProIleGluLysThrIleSerLysAlaLysGly
```

FIG. 4
(continued)

```
1021 CAGCCCCGAGAACCACAGGTGTACACCCTGCCCCCATCCCGGGATGAGCTGACCAAGAAC 1
     GlnProArgGluProGlnValTyrThrLeuProProSerArgAspGluLeuThrLysAsn

1081 CAGGTCAGCCTGACCTGCCTGGTCAAAGGCTTCTATCCCAGCGACATCGCCGTGGAGTGG 1
     GlnValSerLeuThrCysLeuValLysGlyPheTyrProSerAspIleAlaValGluTrp

1141 GAGAGCAATGGGCAGCCGGAGAACAACTACAAGACCACGCCTCCCGTGCTGGACTCCGAC 1
     GluSerAsnGlyGlnProGluAsnAsnTyrLysThrThrProProValLeuAspSerAsp

1201 GGCTCCTTCTTCCTCTACAGCAAGCTCACCGTGGACAAGAGCAGGTGGCAGCAGGGGAAC 1
     GlySerPhePheLeuTyrSerLysLeuThrValAspLysSerArgTrpGlnGlnGlyAsn

1261 GTCTTCTCATGCTCCGTGATGCATGAGGCTCTGCACAACCACTACACGCAGAAGAGCCTC 1
     ValPheSerCysSerValMetHisGluAlaLeuHisAsnHisTyrThrGlnLysSerLeu

1321 TCCCTGTCTCCGGGTAAATGA   1341
     SerLeuSerProGlyLysEnd
```

Vector p11197

Vector p10195

Vector p11201

Summary of the cloning steps of the K-construction

DIAGNOSTIC TEST USING CHIMERIC ANTIBODIES

This application is a continuation of application Ser. No. 07/948,073 filed Sep. 21, 1992, now abandoned, which is a continuation of Ser. No. 07/459,481 filed Jan. 2, 1990, now abandoned.

The invention concerns the use of chimeric monoclonal antibodies or fragments thereof for diagnostic tests.

Since the development of the hybridoma technique for the production of monoclonal antibodies in clinical diagnosis they have been extensively used for immunological determinations. The monoclonal antibodies for this are usually produced in mouse cell lines and therefore, apart from the antigen-specific hypervariable region, only have mouse-specific regions. Such monoclonal antibodies from mice are used for immunological determinations e.g. RIA, IRMA, IEMA. In the diagnosis with the so-called "sandwich" assays e.g. the ELISA (enzyme-linked immunosorbent assay) a substance contained in human blood or serum is detected via two antibodies, one of which is immobilized on a solid phase and the second carries a label. Such a label is usually an enzyme label which can produce a color reaction for the detection.

However, in the past few years falsely increased test values have been identified with increasing frequency in certain patients when using such diagnostic detection methods. Such increased values occur when two circumstances coincide i.e.

a) a sandwich test concept which is based on a linking of two antibodies, i.e. an immobilized antibody on a wall and an antibody carrying a signal, by an antigen and b) the occurrence of so-called heterophilic antibodies or of anti-mouse antibodies in the serum of the patient.

Human heterophilic antibodies are directed against IgG of different animal species, amongst others against mouse IgG, by which means as a rule the test antibodies are affected. Heterophilic antibodies, however, often show cross-reactions with IgG from the rat, cow, sheep, horse, guinea pig or monkeys, less often with IgG from the dog, cat or rabbit. The reason for this seem to be common epitopes in the F(ab')$_2$ fragment (Boscato and Stuart, Clin. Chem. 32 (1988), 1491–1495) or in the Fc part (Clark and Prince, Clin. Chem. 33 (1987), 414) of different IgG molecules.

Such heterophilic antibodies are widespread in humans and probably originate through the use of or injections of animal products. The development of anti-mouse antibodies in humans is also mainly attributable to this.

In the sandwich assays binding of the polyvalent heterophilic antibody or of the anti-mouse antibody to the monoclonal antibodies on the one hand causes a linking of the detection-antibody with the solid phase even in the absence of the antigen which thus produces a false test signal and on the other hand sterically hinders the correct antigen binding of the test antibodies.

It has therefore already been suggested that monoclonal antibodies from different species e.g. from mouse and rat be used in sandwich immunoassays in order to avoid such test interferences (Boscato and Stuart, Clin. Chem. 43, (1988) 27–33). The problem can, however, not be solved by this means since, as has already been mentioned, human heterophilic antibodies are directed against IgG of different animal species. Heterophilic antibodies of many patients react with mouse IgG as well as with rat IgG. Since monoclonal antibodies with a high efficiency can only be obtained at present from the mouse and rat this imposes limitations from the start.

Furthermore, Boscato and Stuart suggested saturating the antibodies of the patient by addition of non-immune IgG of those species from which the monoclonal test antibody is derived in order to avoid false measurement results when testing sera containing heterophilic antibodies. The preparation of such large amounts of mouse antibodies is, however, problematic, expensive and clearly does not lead to the desired result.

It was suggested by Kahn et al., J. Clin. Endocrin. Metabolism., 66 (1988), 526–533 that the heterophilic antibodies contained in the serum be removed by polyethylene glycol precipitation. This is also laborious and can only be used for antigen tests but not, however, for antibody tests. It was furthermore suggested in the same publication that the antibodies used diagnostically be iodinated so that they cannot be recognized any more by the human anti-mouse antibodies. This, however, also requires a lot of time and leads to a loss in activity of the antibodies.

A further suggestion i.e. to remove the heterophilic antibodies with an anti-human immunoglobulin or with protein A (Clin. Chem. 34 (1988), 261–264) is also too complicated for routine determinations and is again only suitable for antigen tests but not for antibody tests.

The object of the invention is therefore to eliminate the interfering effects of heterophilic antibodies in the serum of patients and to enable an undisturbed quantitative determination of substances, antigens as well as antibodies, in the serum of patients.

This object is achieved according to the present invention by the use of chimeric monoclonal antibodies which consist of human antibodies in which the variable regions are completely or partially replaced by the corresponding parts of a non-human monoclonal antibody of the desired specificity or by fragments thereof for diagnostic tests for the quantitative immunological determination of substances in blood or serum of patients.

A human antibody is preferably used as the chimeric antibody in which the variable regions ($V_H$ and $V_L$) have been replaced by the corresponding regions of a non-human monoclonal antibody (e.g. from rat or preferably from mouse). Particularly preferred is the use of a monoclonal human antibody. A human antibody is likewise preferably used as a chimeric antibody in which the hypervariable regions from $V_H$ and $V_L$ have been partially—or particularly preferably—completely replaced by the corresponding regions of a non-human monoclonal antibody (e.g. rat and preferably mouse) (reshaped antibody). Such a preferred antibody thus contains the Fc part, the constant regions of the Fab part as well as the framework regions of the variable regions of a human antibody. The "framework regions" are understood as the four regions of each of the two heavy and of the two light chains of an antibody which surround the three hypervariable regions or are situated between them. The structure of such chimeric antibodies is described for example by Verhoeyen and Riechmann, in Bioessay, Vol. 8, 1988, pages 74 to 78. By the use of chimeric antibodies or fragments thereof according to the present invention the risk of an interaction of the test antibodies with heterophilic antibodies can be largely avoided. The use according to the present invention can be used for all determination procedures which use monoclonal antibodies, for example also for RIA, since also in this procedure there is a risk that test results may be distorted by heterophilic or anti-mouse antibodies. The invention is, however, particularly important and suitable for sandwich assays such as IRMA and IEMA.

Processes for the production of chimeric antibodies in which the variable regions have been replaced are described for example by Brhggemann et al., (1987), J. Exp. Med. 166, 1351–1361, Liu et al., (1987) Proc. Natl. Acad. Sci. USA 84 3439–3443, Whittle et al., Protein Engineering 1 (1987), 499–505, Nature 314 (1985) 452–454, J. Immunol. 137 (1986) 1066–1074, Gene 54 (1987) 33–40 and in WO86/ 01533 as well as in EP-A 0 239 400 and can be adapted by an expert according to the conditions needed for a special test. A slightly modified method for the preparation of a chimeric anti-TSH antibody (MAB<TSH>) is described in the Examples.

Processes for the production of chimeric antibodies in which only the hypervariable regions have been replaced (reshaped antibody) are described in Nature 321 (1986) 522–525 and Nature 332 (1988) 323–327. The preparation of fragments of antibodies can be carried out according to well-known methods, as described for example by Johnstone and Thorpe in Immunochemistry in Practice, Blackwell Scientific, 1982, pages 52 to 53.

In a preferred embodiment of the invention at least one monoclonal antibody or a fragment thereof is used in a diagnostic "sandwich-immunoassay". By this means a linking of both test antibodies can be avoided since at the most the non-chimeric antibody can be bound by heterophilic antibodies or by mouse antibodies, whereas, for the linking both test antibodies need to be bound. In certain cases, especially when relatively large amounts of heterophilic antibodies are present in a patient serum, it may be expedient to use only chimeric antibodies in immunological tests especially in order to avoid competing reactions.

In a preferred embodiment the diagnostic test in which chimeric monoclonal antibodies are used is an enzyme-linked immunosorbent assay (ELISA).

Even though the heterophilic antibodies usually bind to the Fc part of the monoclonal antibodies, in order to avoid any possible interaction it is preferable to use a chimeric antibody in which the variable or hypervariable regions of a human monoclonal antibody are replaced by the corresponding parts of a monoclonal mouse antibody of the desired specificity. By this means the interaction with human anti-mouse antibodies or heterophilic antibodies with cross-reactivity is avoided.

In a preferred embodiment of the invention a chimeric anti-TSH antibody or a fragment thereof is used for the detection of thyroid stimulating hormone (TSH) in patient serum using an ELISA test. For this two complete chimeric genes were reconstructed for the light and heavy chain from the cloned anti-TSH-MAB cDNAs with the aid of two mouse immunoglobulin genes as receptors and the constant regions of one human kappa and of one human gammal gene, these cDNAs were incorporated into an expression vector (Example 1) and expressed in a suitable host cell. The chimeric antibody was then isolated from the nutrient medium according to well known methods.

Thus according to the present invention falsely increased test results due to heterophilic antibodies or anti-mouse antibodies in the serum or blood of patients are successfully prevented in diagnostic immunoassays which use monoclonal antibodies from mice, above all in sandwich assays.

A further embodiment of the invention is thus a process for the diagnostic detection of substances in serum or blood of patients by binding of two monoclonal antibodies $R_1$ and $R_2$ directed against the substance, of which the first antibody $R_1$ is capable of binding to a solid phase or is already bound and the second antibody $R_2$ carries a label, binding of the antibody $R_1$ to the solid phase if desired, separation of the complex formed of $R_1$, substance and $R_2$ which is bound to the solid phase and detection via the labelling of the antibody $R_2$, whereby a chimeric monoclonal antibody or a fragment thereof is used at least for one of the antibodies $R_1$ or $R_2$.

The expression "capable of binding to a solid phase" also means, within the scope of the invention, inter alia that the antibody $R_1$ can be fixed to the solid phase via an additional component such as e.g. a third antibody bound to the solid phase which is directed against the Fc part of $R_1$, or a biotin molecule bound to $R_1$ and streptavidin bound to the solid phase.

In this connection exemplary variants of the test method consist inter alia of a) the use of an antibody bound to a solid phase against the Fc fragment of a human antibody which binds the Fc part of a chimeric human antibody directed against the antigen, and labelling of the complex via e.g. a peroxidase labelled second antibody which is likewise directed against the antigen;

b) the use of streptavidin bound to a solid phase, a biotinylated chimeric antibody directed against the antigen as well as a second labelled antibody which is likewise directed against the antigen;

c) the use of an antibody bound to a solid phase against the Fcγ part of a mouse antibody, a mouse antibody capable of binding to it and which is directed against the antigen and of a labelled chimeric antibody directed against the antigen;

d) the use of streptavidin bound to a solid phase, a biotinylated mouse antibody directed against the antigen and of a labelled chimeric antibody which is likewise directed against the antigen;

e) the use of a chimeric antibody bound to a solid phase which is directed against the antigen and of a labelled mouse antibody which is likewise directed against the antigen; or f) the use of a mouse antibody bound to a solid phase which is directed against the antigen and of a labelled chimeric antibody which is likewise directed against the antigen.

In the process according to the present invention the label of the one antibody can be a radioactive label as well as another type of label such as e.g. an enzymatic label. In accordance with the invention it is preferable to use an enzyme label which in turn is detected by a color reaction caused by the enzyme.

In this connection the labelling can also be indirect via a biotin bound to the respective antibody and a label bound to streptavidin, e.g. peroxidase. The wall of a reaction vessel can for example be used as the solid phase.

In all the variants mentioned instead of using whole antibodies it is also possible to use only certain fragments of these antibodies and an embodiment of the present invention.

In a preferred embodiment two chimeric monoclonal antibodies are used for the process according to the present invention. By this means a further increase in the reliability of the test results is achieved especially when high concentrations of heterophilic antibodies are present.

The process according to the present invention using chimeric monoclonal antibodies can also be used for diagnostic tests which are not based on the formation of a sandwich of antibodies and substance to be detected such as e.g. RIA since also in such tests there is a risk that the test results may be falsified by the presence of heterophilic antibodies, however it is of particular importance in sandwich immunoassays.

The production of monoclonal antibodies can be carried out according to the well known methods which have already been cited.

By means of the invention interferences in diagnostic tests caused by heterophilic antibodies or anti-mouse antibodies in the serum or blood of patients can be successfully avoided in a simple and effective manner. The necessity to add non-specific, non-immune IgG from the species from which the monoclonal antibodies were isolated or of a time-consuming precipitation of the heterophilic or anti-mouse antibodies as suggested by the state of the art can be avoided according to the present invention and even a significantly increased accuracy of the test results can be achieved.

The following Examples in conjunction with the Figures elucidate the invention further.

FIG. 1 shows the DNA and amino acid sequence of the kappa chain of a monoclonal antibody against TSH;

FIG. 2 shows the DNA and amino acid sequence of the gamma chain of a monoclonal antibody against TSH;

FIG. 3 shows the DNA and amino acid sequence of the kappa chain of a chimeric monoclonal antibody against TSH;

FIG. 4 shows the DNA and amino acid sequence of the gamma chain of a chimeric monoclonal antibody against TSH;

Figure 5:
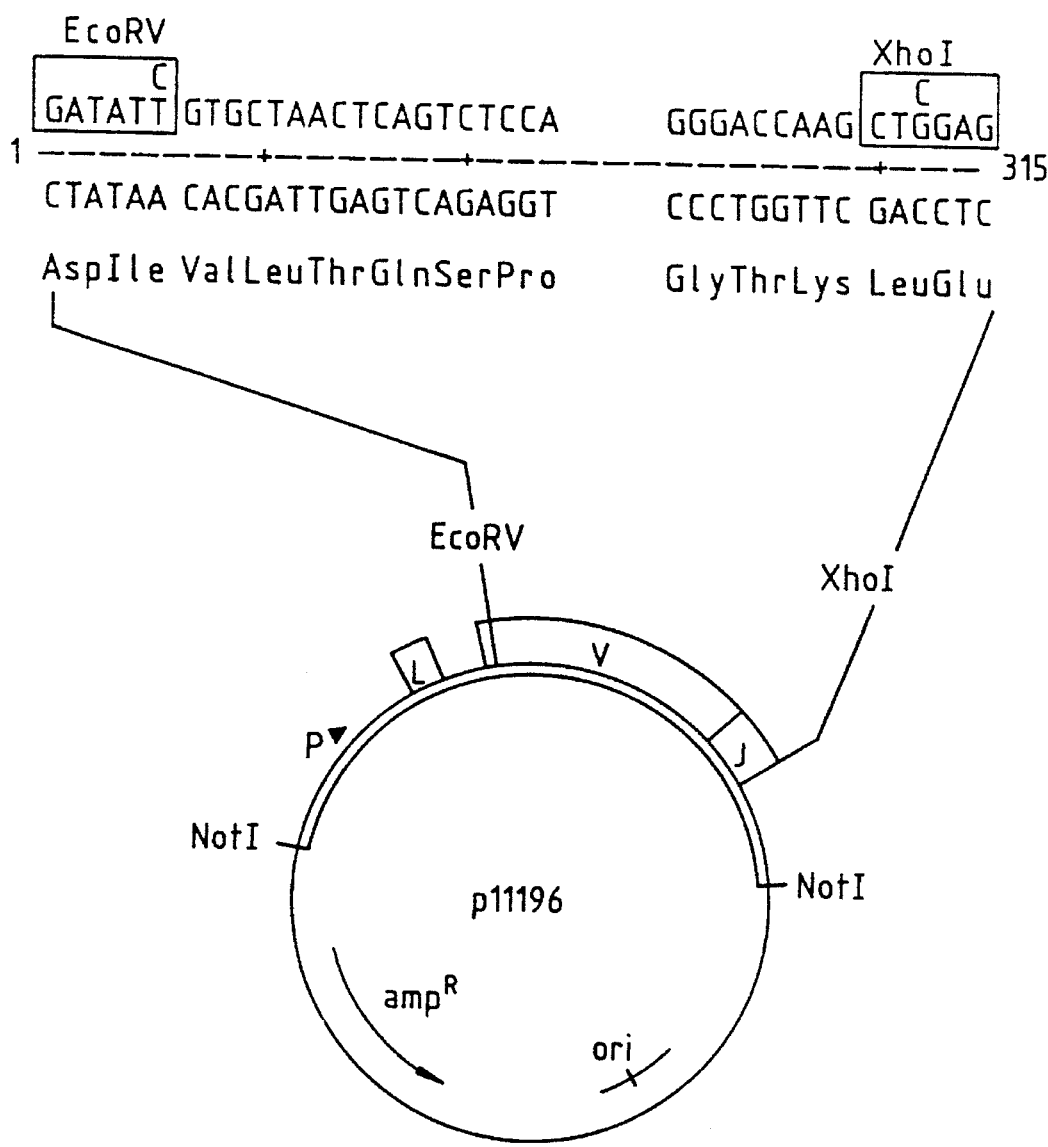

FIG. 5 shows the vector p11196. Vector p11196 was constructed on the basis of the pUC vectors (C. Yanisch-Perron et al., Gene 33, (1985), 103–119) (nucleotide position 630 to 2675 of pUC18). The NotI fragment (▢) carries the functional rearranged V region of a K gene of the mouse. An EcoRV cleavage site was introduced at the beginning of the V region and a XhoI cleavage site at the end of the J region by mutagenesis (nucleotide position 6 or 312 respectively).

Figure 6:
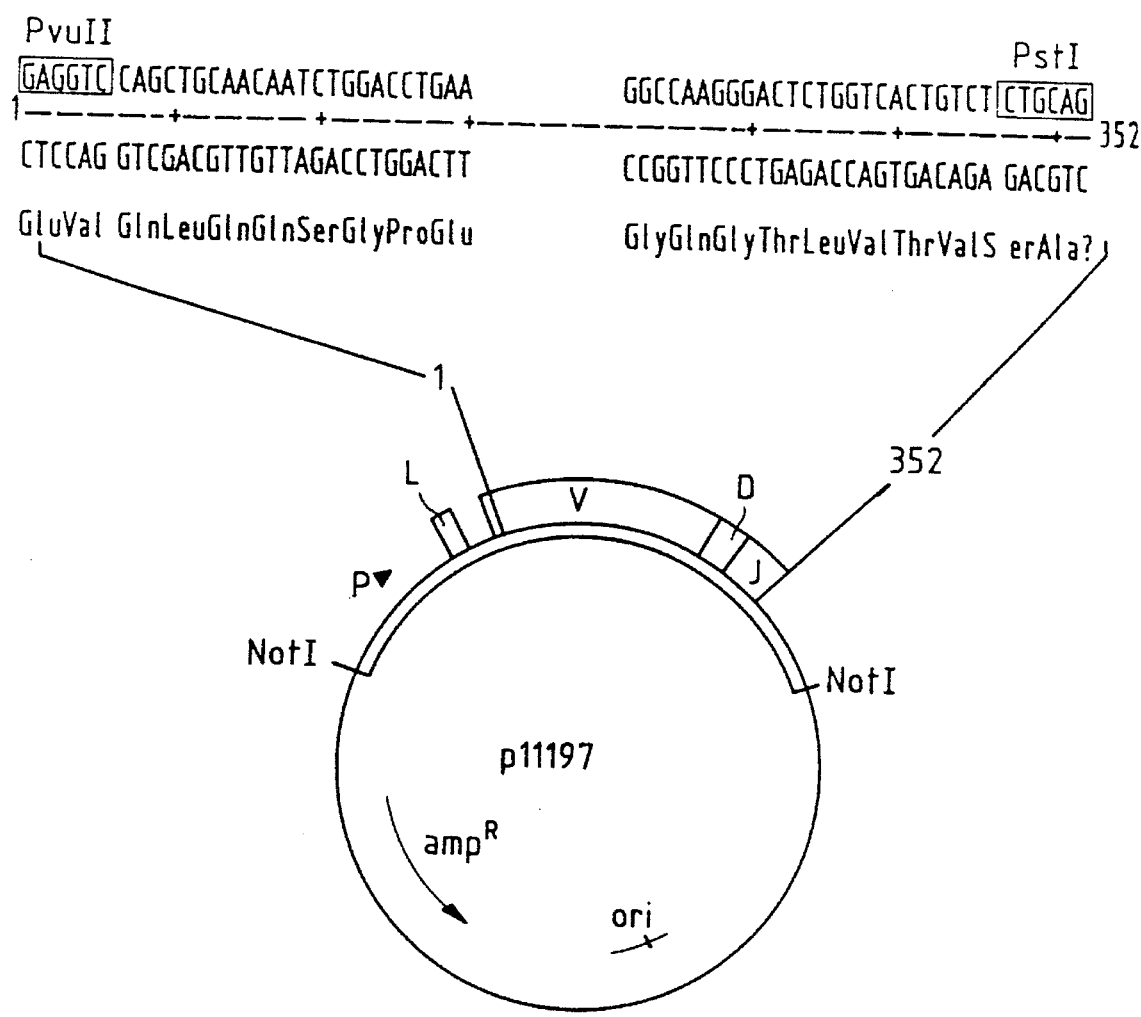

FIG. 6 shows the vector p11197. Vector p11197 was constructed on the basis of the pUC vectors (C. Yanisch-Perron et al., Gene 33, (1985), 103–119) (nucleotide position 630 to 2675 of pUC18). The NotI fragment (▢) carries the VDJ region of a functional rearranged $\gamma_1$ gene of the mouse.

Figure 7:
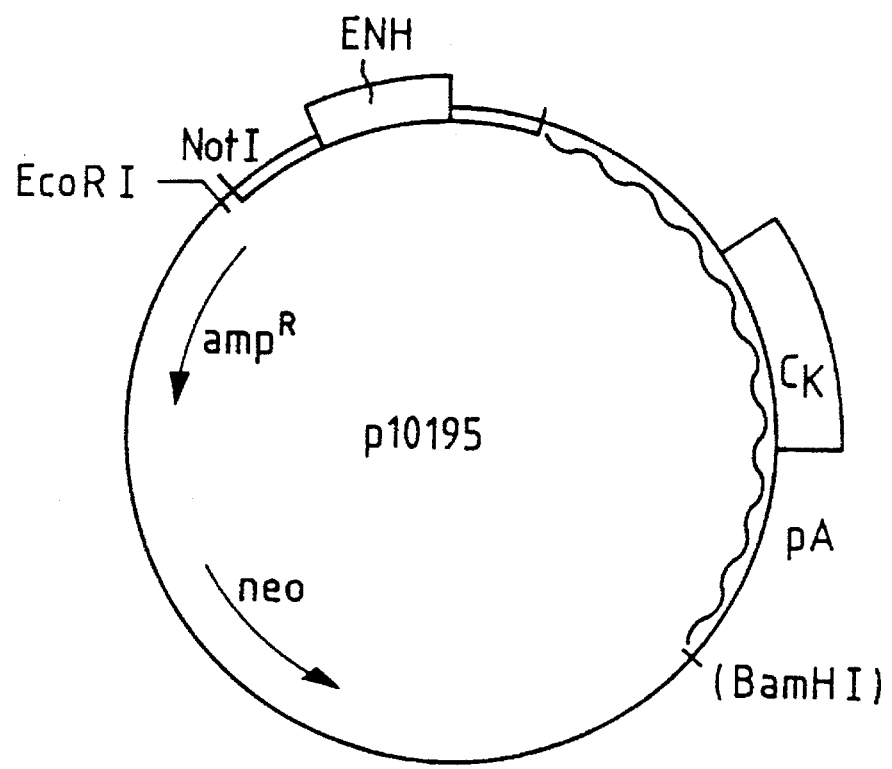

FIG. 7 shows the vector p10195. Vector p10195 was constructed on the basis of pSV2 neo (R.C. Mulligan and P. Berg (1981), Proc. Nat. Acad. Sci. USA 78, 2072–2076). A DNA fragment containing the K enhancer of the mouse (▢) as well as a DNA fragment containing the constant region of a human K gene (▭) were cloned between its EcoRI and BamHI cleavage sites. This resulted in the loss of the BamHI cleavage site.

Figure 8:
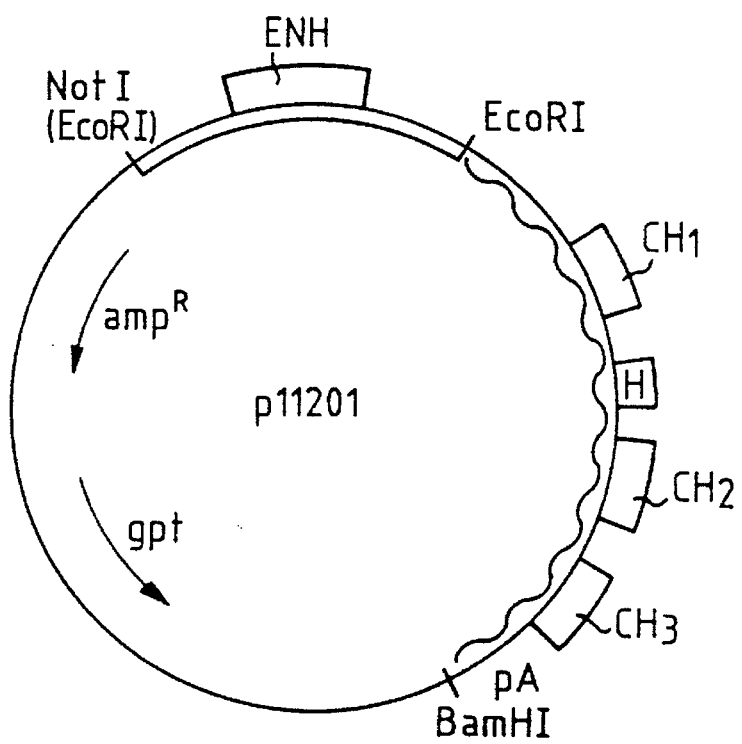

FIG. 8 shows the vector p11201. Vector p11201 was constructed on the basis of pSV2gpt (R.C. Mulligan and P. Berg (1981), Proc. Nat. Acad. Sci. USA 78, 2072–2076). A DNA fragment containing the enhancer of the heavy immunoglobulin chains of the mouse (▢) as well as a DNA fragment containing the constant region of a human $\gamma_1$ gene (▭) were cloned between its EcoRI and BamHI cleavage sites. In this process the EcoRI cleavage site from pSV2gpt was converted into a NotI cleavage site.

Figure 9:
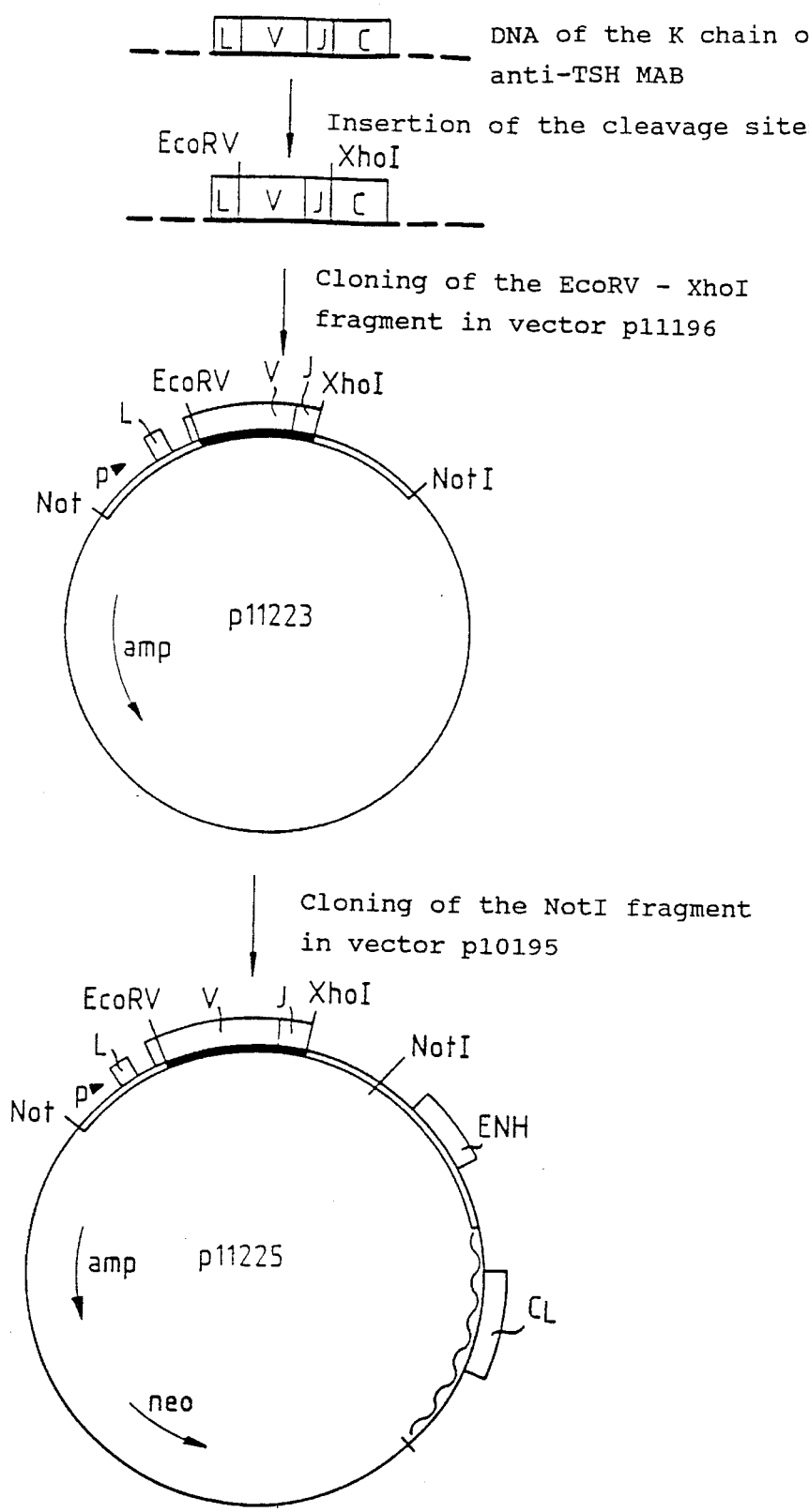
Figure 10:
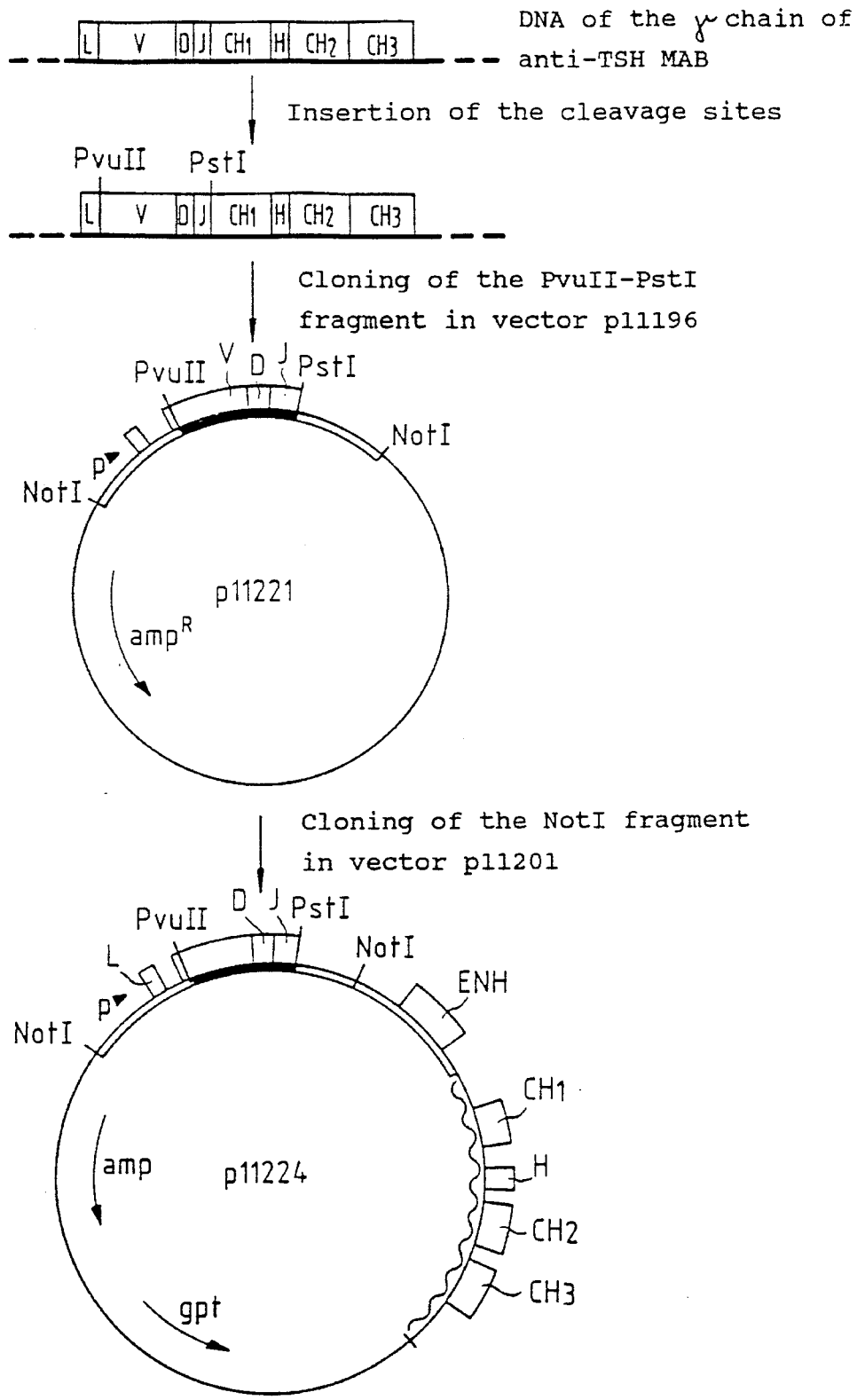
Figure 11:
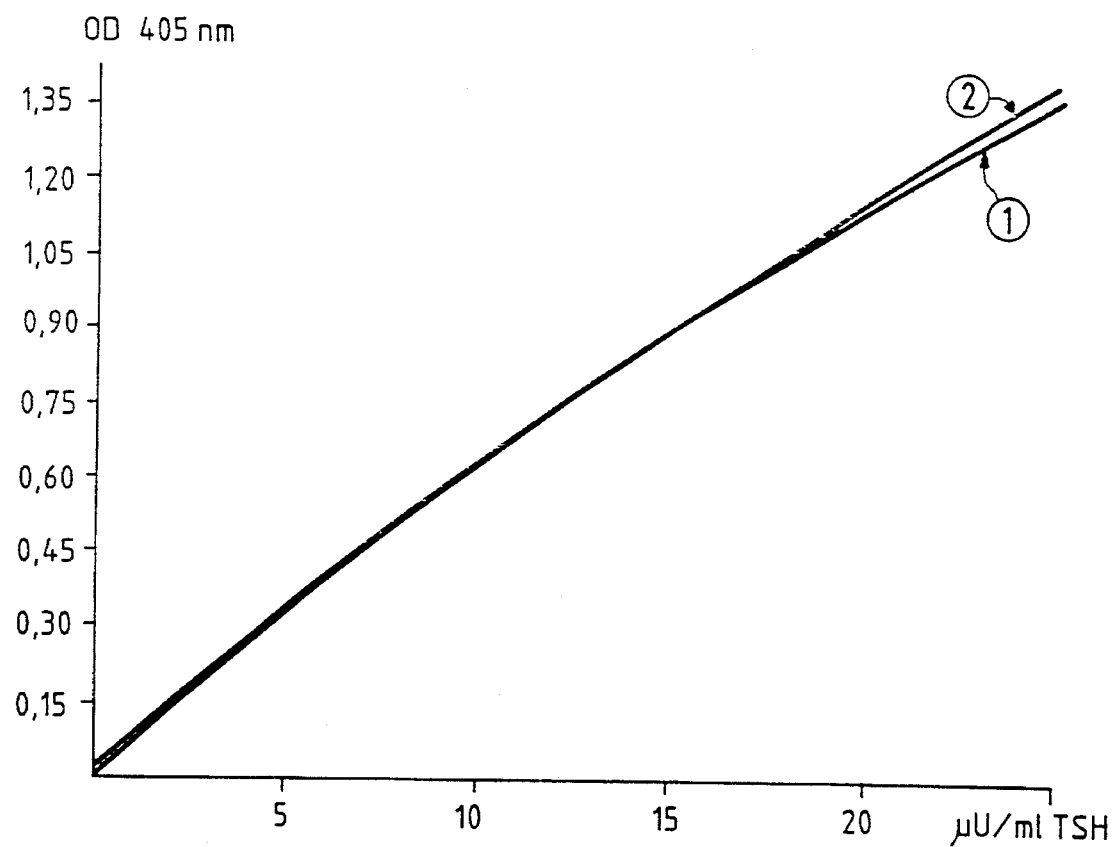

FIG. 9 and 10 show the cloning steps of the kappa and gamma chain construction;

FIG. 11 shows a comparison of the standard curves for a TSH monoclonal antibody, curve 2 (FIG. 1 and 2) and for a chimeric anti-TSH antibody, curve 1 (FIG. 3 and 4, Example 1). OD: optical density, absorbance.

EXAMPLE 1

Production of a chimeric antibody against TSH (chimeric monoclonal antibody, chimeric anti-TSH MAB)

a) Construction of vector p11196 (FIG. 5)

A 1.8 Kb long XbaI fragment from the K gene of the anti-idiotypic MAB A2044 (F. Sablitzky et al., (1985), EMBO J. 4, 345–350) was filled up at the ends with the Klenow fragment of DBA-Polymerase I, provided with NotI linkers (5'GCGGCCGC3') and cloned in pUC18 which had been cleaved with DraII/PvuII (Yanisch-Perron, C, G. Vieira and G. Messing, Gene 33 (1985) 103–119) and whose ends had likewise been filled up and provided with NotI linkers (T. Maniatis, E. F. Fritsch and J. Sambrook (1982), Molecular Cloning—A Laboratory Manual; Cold Spring Harbor Laboratory).

b) Construction of vector p11197 (FIG. 6)

A 1 Kb long EcoRI/HindIII fragment from the $\gamma$l gene of the anti-idiotypic MAB A2044 (F. Sablitzky et al., (1985), EMBO J. 4, 345–350) was filled up at the ends, provided with NotI linkers and cloned in the vector pUC18 (Yanisch-Perron, C, G. Vieira and G. Messing, Gene 33 (1985) 103–119) which had been cleaved with DraII/PvuII and treated in the same way.

c) Oligonucleotide directed mutageneses

In the DNA sequence of FIG. 1 an EcoRV cleavage site was inserted at position 1 with the aid of the oligonucleotide I and a XhoI cleavage site was inserted at position 325 (oligonucleotide II). The nucleotides 1 to 9 of the oligonucleotide I are homologous to the leader peptide region of the kappa chain of the anti-TSH MAB which is not included in FIG. 1. FIG. 1 shows the mature kappa chain of the MAB. In the DNA sequence of FIG. 2 a PvuII cleavage site was inserted at position 7 (oligonucleotide III) and a PstI cleavage site at position 344 (oligonucleotide IV). In the sequence of the VJ region of the K gene of MAB A2044 in p11196 (F. Sablitzky et al., (1985), EMBO J. 4, 345–350) an EcoRV cleavage site was inserted at position 1 (oligonucleotide V) and a XhoI cleavage site at position 310 (oligonucleotide VI) (FIG. 5). All mutageneses were carried out according to the "gapped-duplex" method of Inouye et al., (Synth. Appl. DNA RNA; (1987), Ed. S. A. Narang; Academic Press; 181–206) starting from plasmid DNA.

Oligonucleotides used:

I: 5'ACCAACGGTGATATCGTGATGACCCAG3'

II: 5'GGCACCAAGCTCGAGATCAAACGG3'

III: 5'ATGAGCAGCTGCAAGAGTCAGGAC3'

IV: 5'GTCACCGTCTCTGCAGCCAAAACG3'

V: 5'GATATCGTGCTAACTCAGTCTCCA3'

VI: 5'GCTGCTGGGACCAAGCTCGAGCTG3' d) Construction of vector p10195 (FIG. 7)

A 2 Kb EcoRI/-Asp700 fragment (Asp700 converted by linker in BamHI) which contains the enhancer region (Nature 307 (1984) 80–82) of the K gene of MAB A2044 was cloned in the plasmid pSV2neo (R. C. Mulligan, P. Berg (1981), Proc. Nat. Acad. Sci. USA 78, 2072–2076) which had been cleaved with EcoRI and BamHI, a 2.8 Kb EcoRI fragment (also filled up) from pC1 (H.-G. Klobeck et al., (1984), Nucl. Acids Res. 12, 6995–7006) which contains the constant region of a human K gene was cloned. A XbaI cleavage site located upstream of the mouse K enhancer of the resulting plasmid was converted into a NotI cleavage site by insertion of a linker (FIG. 7).

e) Construction of vector p11201 (FIG. 8)

A 7 Kb HindIII fragment which contained the constant regions of a human $\gamma$l gene ($\gamma$l-10) (N. Takahashi et al., (1982), Cell 29, 671–679) was cloned in the plasmid pSV2gpt (R. C. Mulligan, P. Berg (1981), Proc. Nat. Acad. Sci. USA 78, 2072–2076) which had been cleaved with EcoRI and BamHI. (This original HindIII fragment was converted into an EcoRI-BamHI fragment by filling up the HindIII ends and intermediate cloning in the Asp718 cleavage site of pUC19 (C. Yanisch-Perron et al., (1985), Gene 3, 103–119) which was also filled up). A 1.6 Kb HindIII-EcoRI fragment containing the enhancer region (Cell 41 (1985)

885–897) of the γl gene of MAB A2044 (F. Sablitzky et al., (1985), EMBO J. 4, 345–350) was inserted in the same orientation into the EcoRI cleavage site of the resulting plamid. In this process the HindIII cleavage site was converted into a NotI cleavage site as well as adapted to the EcoRI cleavage site with the aid of an adaptor (5'AAT-TGCGGGCCGC3' hybridized with 5'AGCTGCGGC-CGC3') (FIG. 8).

f) Assembly of the expression plasmid for the light chain of the chimeric antibody The DNA of FIG. 1 was cleaved by EcoRV and XhoI at the cleavage sites introduced by mutagenesis. The 323 bp fragment corresponding to the V region was cloned in the vector p11196 which had also been similarly cleaved with EcoRV and XhoI. The resulting vector p11223 was cleaved with NotI; the 1.8 Kb fragment corresponding to the immunoglobulin part was isolated and cloned in the vector p10195, which had been cleaved with NotI (FIG. 9). The resulting vector p11225, DSM 5094 was purified by CsCl density gradient centrifugation (T. Maniatis et al., (1982), Molecular Cloning—A Laboratory Manual; Cold Spring Harbor Laboratory).

g) Assembly of the expression plasmid for the heavy chain of the chimeric antibody The cDNA of FIG. 2 was cleaved by PvuII and PstI at the cleavage sites introduced by mutagenesis. As a result of an internal PstI cleavage site two fragments corresponding to the V region are formed of 231 bp and 103 bp. Both fragments were cloned in their original orientation in the vector p11197 which had also been cleaved with PvuII and PstI. The resulting vector p11221 was cleaved with NotI. The 1 Kb large NotI fragment corresponding to the immunoglobulin part was cloned in the NotI cleavage site of vector p11201 (FIG. 10). The resulting vector p11224, DSM 5093 was purified by CsCl density gradient centrifugation (T. Maniatis et al., (1982), Molecular Cloning—A Laboratory Manual; Cold Spring Harbor Laboratory).

h) Transfection of mammalian cells with the expression plasmids

Vector p11224, DSM 5093 as well as vector p11225, DSM 5094 were linearized at their single PvuI cleavage site (in the bacterial amp$^R$ gene). Sp2/0 Ag14 cells (ATCC CRL1581) were cultured on RPMI medium (G. E. Moore, R. E. Gerner & H. A. Franklin (1967) Culture of Normal Human Leucocytes. J.A.M.A. 199, 519–526) which was supplemented with 10% foetal calf serum, 20 mmol/l glutamine, 1 mmol/l Na pyruvate, 20 μg/ml 8-azaguanine and amino acids (MEM amino acids, for composition see R. G. Ham, (1963) Exp. Cell. Res. 29, 515–526). Cells which grew exponentially (approx. 5×10$^5$/ml) were resuspended to 1.25×10$^6$/ml in 1× HeBS buffer (G. Chu et al., (1987), Nucl. Acids Res. 15, 1311–1326). Linearized vector p11224 and p11225, DSM 5094 were each added in a concentration of 12.5 μg/ml. Cells and DNA were preincubated for 10 minutes at 0° C. and 800 μl aliquots were subsequently subjected to a single electrical impulse of 230 V (Bio Rad Gene Pulser) and then incubated for a further 10 minutes at 0° C.

Afterwards the cells (as described, however without 8-azaguanine) were plated in RPMI on cloning plates.

24 hours after the transfection they were selected with G418 (Geneticin Gibco, 1 mg/ml) or G418 and additionally mycophenolic acid (in three increasing steps from 250 ng/ml to 500 ng/ml to 2 μg/ml). Using both methods of selection clones were obtained that contained vector p11224, DSM 5093 as well as vector p11225, DSM 5094 and actively expressed chimeric anti-TSH MAB (ECACC 88091403).

The amino acid and DNA sequence of the kappa and gamma chain of the chimeric anti-TSH MAB are shown in FIG. 3 and 4.

The hybridoma cell line which produces the chimeric anti-TSH MAB is deposited at the European Collection of Animal Cell Culture, Porton Down, GB under the number ECACC 88091403.

The following chimeric MAB's can be prepared in an analogous way:

| starting with the cDNA of a MAB (mouse) from cell lines | chimeric MAB |
| --- | --- |
| ECACC 84122006 | against follicle stimulating hormone (FSH) |
| ECACC 84122001 | against luteinizing hormone (LH) |
| ECACC 85121701 | against testosterone |

EXAMPLE 2

Function test for the chimeric anti-TSH MAB in a double-MAB sandwich test a) Anti-TSH MAB A MAB was used as the anti-TSH MAB whose amino acid sequences of the kappa and gamma chains are shown in FIG. 1 and 2.

b) Preparation of a peroxidase conjugate of a TSH-binding mouse antibody which is complementary to the anti-TSH MAB (FIG. 1 and 2).

The IgG fraction of the monoclonal anti-TSH antibody, ECACC 87122202, was purified from ascites fluid by ammonium sulphate precipitation and chromatography on a DEAE ion exchanger according to A. Johnstone and R. Thorpe, Immunochemistry in Practice, Blackwell Scientific, 1982, pages 44 to 45. 90 mg Fab fragments were prepared from 200 mg IgG according to the method of Johnstone and Thorpe ibid. pages 52 to 53. 50 mg of the Fab fragments was reacted with S-acetyl-thio-succinic acid anhydride and coupled with 50 mg prepolymerized maleinimido-hexanoyl peroxidase according to the method described in DE-A-38 25 735, Example 8.2. A conjugate pool was obtained with a molecular weight from 2 to 3 million by AcA 22 chromatography. Yield 31 mg protein with 13500 U peroxidase (POD) activity.

c) Procedure for the function test

1. Reference ELISA (enzyme-linked immunosorbent assay) with anti-TSH MABs

Step 1:

The wells of a microtitre plate were coated (two hours, 25° C.) with 5 μg/ml polyclonal sheep (anti-mouse Fcγ) IgG (immunosorbed) by spontaneous adsorption and recoated with 1% crotein C in 50 mM HEPES buffer/150 mM NaCl, pH 7.0 (30 minutes at 25° C.) to saturate the remaining adsorption sites.

Step 2

0.2 ml anti-TSH MAB (Example 2a) at a concentration of 50 ng IgG/ml dissolved in RPMI cell culture medium was pipetted into each of the emptied wells and incubated for 60 minutes at room temperature. Buffer without MAB-IgG was used for controls.

Step 3:

After washing three times with buffer A, 40 μl TSH standard solution or patient serum (with interfering factors, diluted 1+1 in buffer B) together with 200 μl buffer B were pipetted into each well and incubated for 60 minutes at room temperature.

The TSH standard solutions were prepared by supplementing bovine serum with a solution of TSH. The resulting TSH concentrations of the various supplemented standard solutions were assigned by measurement with a commercial TSH test (Enzymun-Test$^R$ TSH, Boehringer Mannheim GmbH, Order No. 736 082).

Step 4:

After washing twice with buffer A each well was filled with 0.2 ml enzyme-conjugate solution (Example 2b) with 100 mU/ml POD activity (dilution of the conjugate concentrate from b) in buffer C). The conjugate was incubated for 60 minutes at room temperature.

Step 5:

After washing three times with buffer C each well was filled with 0.2 ml ABTS® substrate (2,2'-azino-di-[3-ethyl-benzthiazoline sulphonate] 1.9 mmol/l ABTS®, 100 mmol/l phosphate citrate buffer, pH 4.4, sodium perborate 3.2 mmol/l) and incubated for 60 minutes at room temperature.

The absorbance values of the resulting dye solutions in the wells were measured at 405 nm with a photometer suitable for microtitre plates.

Buffer A:

16 mmol/l potassium phosphate buffer, pH 6.9

0.2% bovine serum albumin 0.15 mol/l NaCl 0.1% bovine IgG

Buffer B:

Buffer A with the addition of 0.1% sheep IgG.

Buffer C:

36 mmol/l potassium phosphate buffer, pH 6.9

0.2% bovine serum albumin 0.15 mol/l NaCl

2% Dextran T500

0.01% phenol (concentrations are the final concentrations in the test)

ELISA test with chimeric anti-TSH MAB (Example 1)

The test procedure with the chimeric MAB follows exactly the steps of the reference test c)1. with the following specific changes:

In step 1, polyclonal sheep(anti-human Fcγ) IgG (immunosorbed) was coated. In step 2, a dilution of cell culture supernatant with 50 ng chimeric anti-TSH MAB/ml was pipetted.

The concentration of chimeric anti-TSH MAB was determined with a human Fcγ-specific microtitre ELISA.

FIG. 11 shows a comparison of the standard curves for the test with anti-TSH MAB (Example 2c1) (curve 2) and the test with chimeric anti-TSH MAB (Example 2c2) (curve 1). The course of the calibration curves is, within the limits of error, identical. It follows from this that the TSH binding site in the chimeric MAB is unchanged and that the Fcγ part of the chimeric MAB responds in the same way as that of human IgG.

As a control a microtitre plate coated according to Example 2c1 with sheep(anti-mouse Fcγ) IgG was used in the test according to Example 2c2. As expected the resulting absorbances for the standard samples were not different from the blank values.

Table 1 shows the measured values for three different patient sera (PS 71, PS 92, PS 99) which were known to yield falsely increased values in the mouse double-MAB immune test. The sample PS 107, a normal human serum with <0.5 μU TSH/ml and without interfering factors, was also tested as a control.

The resulting absorbances in both test systems for the serum samples were converted on the respective standard curve to μU TSH/ml sample.

As a control that in the test system with chimeric anti-TSH MAB a defined amount of TSH was correctly recovered in human sera with interfering factors, each of the sera was supplemented with 20 μU TSH/ml and also measured.

TABLE 1

Results of function tests with anti-TSH MAB and chimeric anti-TSH MAB

1. Test system using a coating of sheep (anti-mouse Fcγ)

| Sample | Anti-TSH MAB (Example 2c1) | Absorbance Δ A$_{405}$ (against blank) | μU TSH/ml |
|---|---|---|---|
| PS 71 | + | 0.585 | 19.2 |
|  | − | 0.015 |  |
| PS 92 | + | 0.268 | 8.0 |
|  | − | 0.008 |  |
| PS 99 | + | 0.550 | 17.6 |
|  | − | 0.022 |  |
| Normal serum 107 | + | 0.015 | <0.5 |
|  | − | 0.005 |  |

2. Test system using a coating of sheep (anti-human Fcγ)

| Sample | Chimeric Anti-TSH MAB (Example 2c2) | Absorbance Δ A$_{405}$ | μU/ TSH/ml |
|---|---|---|---|
| PS 71 | + | 0.00 | 0.5 |
|  | − | 0.00 |  |
| PS 92 | + | 0.045 | 1.2 |
|  | − | 0.00 |  |
| PS 99 | + | 0.015 | <1.0 |
|  | − | 0.01 |  |
| PS 71 + 20 μU TSH/ml | + | 0.603 | 19.4 |
| PS 92 + 20 μU TSH/ml | + | 0.678 | 22.1 |
| PS 99 + 20 μU TSH/ml | + | 0.641 | 20.8 |
| zero standard + 20 μU TSH/ml | + | 0.622 | 20.2 |

The TSH concentrations of the patient sera were measured with an Enzymun TSH test kit (Boehringer Mannheim GmbH, order no, 7 36082). This test is not interfered with by anti-mouse IgG interfering factors since it contains a conjugate of a Fab fragment of a polyclonal anti-TSH antibody from sheep and peroxidase instead of a conjugate of a Fab fragment of an anti-TSH antibody from mouse and peroxidase.

Values found: PS 71 (0.52 μU/ml), PS 92 (2.2 μU/ml), PS 99 (0.9 μU/ml).

From the values in the Table it is obvious that the test system according to Example 1c1 finds apparent TSH contents in the patient sera with interfering factors which are falsely grossly increased. By use of the chimeric anti-TSH MABs in a test system which is in all other respects completely analogous (Example 2c2) this interference is completely eliminated. Genuinely increased TSH-contents are correctly recovered within the limits of error.

We claim:

1. A process for the suppressive of inteverences in the diagnostic detection of a substance in a patient's serum or blood by binding two monoclonal antibodies $R_1$ and $R_2$, or Fab fragments, Fab' fragments or F(ab')2 fragments thereof to the substance, comprising the steps of:

contacting $R_1$ and $R_2$, or Fab fragments, Fab' fragments or F(ab')2 fragments thereof, with the blood or serum of a patient, to form a complex between $R_1$ or a Fab fragment, Fab' fragment or F(ab')2 fragment thereof, the substance, and $R_2$ or a Fab fragment, Fab' fragment or F(ab')2 fragment thereof; wherein $R_1$ or a Fab fragment, Fab' fragment or F(ab')2 fragment thereof is capable of binding to a solid phase or is bound to said solid phase and $R_2$ or a Fab fragment, Fab' fragment or F(ab')2 fragment thereof is labeled, and detecting the formation of said complex via said label, wherein at least one of said monoclonal antibodies $R_1$ and $R_2$ is a chimeric monoclonal antibody comprising a human antibody in which variable regions of said human antibody are completely replaced by corresponding parts of a non-human monoclonal antibody of the desired specificity.

2. The process according to claim 1, wherein both $R_1$ and $R_2$ are chimeric monoclonal antibodies or a Fab fragment, a Fab fragment, Fab' fragment or F(ab')2 fragment thereof.

3. The process according to claim 1, wherein said chimetic monoclonal antibody comprises (i) variable regions of a monoclonal mouse antibody of the desired specificity and (ii) constant regions of a Fab part and a Fc part of a monoclonal human antibody.

4. The process according to claim 1, wherein said chimeric monoclonal antibody comprises (i) hypervariable regions of a monoclonal mouse antibody, (ii) Fc part of a human monoclonal antibody (iii) constant regions of a Fab part of said human monoclonal antibody and (iv) framework regions from variable regions of said human monoclonal antibody.

5. The process according to claim 1, wherein said label is an enzyme label.

6. The process according to claim 1, wherein said process is an immuno-radiometric (IRMA) or immuno-enzymatic (IEMA) assay.

7. The process according to claim 6, wherein said immuno-enzymatic assay is an enzyme-linked immunosorbent assay (ELISA).

8. A diagnostic composition for the quantitative immunological determination of a substance in a patient's blood or serum, comprising chimeric anti-TSH monoclonal antibodies, wherein said antibodies are human antibodies in which the variable regions are completely or partially replaced by corresponding parts of a non-human monoclonal antibody.

* * * * *